(12) United States Patent
Yawata et al.

(10) Patent No.: US 6,605,040 B2
(45) Date of Patent: Aug. 12, 2003

(54) ULTRASONIC DIAGNOSTIC APPARATUS

(75) Inventors: Tsutomu Yawata, Tokyo (JP); Naoto Sato, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/300,340

(22) Filed: Nov. 20, 2002

(65) Prior Publication Data

US 2003/0105400 A1 Jun. 5, 2003

(30) Foreign Application Priority Data

Nov. 29, 2001 (JP) ......................................... 2001-364501

(51) Int. Cl.[7] .................................................. A61B 8/00
(52) U.S. Cl. ........................ 600/437; 345/173; 358/1.15
(58) Field of Search ................................. 600/437, 441, 600/455; 345/177, 173; 358/1.15; 178/18.04; 333/138; 378/92, 62

(56) References Cited

U.S. PATENT DOCUMENTS

| | | | |
|---|---|---|---|
| 5,477,858 A | * 12/1995 | Norris et al. | ................ 600/441 |
| 5,657,053 A | * 8/1997 | Files et al. | .................. 345/177 |
| 5,657,054 A | 8/1997 | Files et al. | |
| 6,053,906 A | 4/2000 | Honda et al. | |
| 6,097,788 A | * 8/2000 | Berenstein et al. | ........... 378/92 |
| 2002/0080392 A1 | * 6/2002 | Parvulescu et al. | ........ 358/1.15 |

* cited by examiner

Primary Examiner—Marvin M. Lateef
Assistant Examiner—Ruby Jain
(74) Attorney, Agent, or Firm—Carl B. Horton, Esq.; Armstrong Teasdale LLP

(57) ABSTRACT

For the purpose of providing an ultrasonic diagnostic apparatus for improving ease of operation by effectively utilizing two display devices, at least two display modes are defined. In the first display mode, arithmetic control/signal processing means 11 controls video signal processing means 18 to display an ultrasonic diagnostic image based on ultrasonic reflection signals stored in an image memory 16 on a CRT device 30 as a monitor display device, and controls video signal processing means 17 to display operation-indicating items for the operation relating to ultrasonic diagnosis on an LCD device 40, and conducts task processing for ultrasonic diagnosis in response to an operation detected by position detecting means in a touch panel 42. In the second display mode, the arithmetic control/signal processing means 11 controls the video signal processing means 18 to display operation-indicating items for the operation relating to ultrasonic diagnosis on the CRT device 30, and controls the video signal processing means 17 to display an ultrasonic diagnostic image based on ultrasonic reflection signals stored in the image memory 16 on the LCD device 40, and conducts processing in response to a position detection signal detected by the position detecting means in the touch panel 42, for example, conducts zoom processing.

25 Claims, 11 Drawing Sheets

ULTRASONIC DIAGNOSTIC APPARATUS

CROSS REFERENCE TO RELATED APPLICATIONS

This application claims the benefit of Japanese Application No. 2001-364501 filed Nov. 29, 2001.

BACKGROUND OF THE INVENTION

The present invention relates to an ultrasonic diagnostic apparatus.

FIG. 9 is a schematic configuration diagram of a conventional ultrasonic diagnostic apparatus.

The ultrasonic diagnostic apparatus 100A illustrated in FIG. 9 comprises an ultrasonic probe (search unit) 1, transmitting/receiving means 2, signal processing means 3, ultrasonic signal processing means 50, a CRT device 30A, a keyboard (KB) 31, a liquid crystal display (LCD) device 40A, and a touch panel 42A provided over the front surface of a display portion of the LCD device 40A.

The ultrasonic diagnostic apparatus 100A may comprise a trackball 32 and a mouse 33, but they are not essential.

The ultrasonic diagnostic apparatus 100A further comprises a printer device 60.

The ultrasonic signal processing means 50 has a cine memory 51, a digital scan converter (DSC) 52, image processing means 53, first control means 54, and a status table 55. The ultrasonic signal processing means 50 further has second control means 56, a touch sensor interface (I/F) 57, and graphic processing means 58.

The CRT device 30A, LCD device 40A and KB 31 are disposed as exemplarily shown in FIGS. 2(A) and (B).

The CRT device 30A is placed above an operation panel of the ultrasonic diagnostic apparatus, and is disposed at a position facing a physician or a technician (referred to as an operator hereinbelow) who sits down in front of the operation panel of the ultrasonic diagnostic apparatus 100A and operates the ultrasonic probe 1 on a subject. The CRT device 30A displays information as exemplarily shown in FIG. 10. Details of the display illustrated in FIG. 10 will be described later.

The touch panel 42A is made of a transparent piezoelectric sheet, through which the items displayed on a display screen of the LCD device 40A can be viewed. A press of the touch panel 42A by a finger, a pencil or the like generates a voltage at the pressed portion. By detecting the portion generating the voltage as two-dimensional coordinates by position detecting means (not shown), the pressed portion in the display screen of the LCD device 40A can be detected. Thus, the LCD device 40A and touch panel 42A are used as interactive means for the operation of the ultrasonic diagnostic apparatus.

The LCD device 40A allows the operator to view the displayed items, and to issue commands for the operation of the ultrasonic diagnostic apparatus via the display portion of the LCD device 40A. Accordingly, the LCD device 40A is disposed within arm's reach of the operator on the operation panel of the ultrasonic diagnostic apparatus below the CRT device 30A.

The KB 31 is used to supplement the interactive operation conducted on the LCD device 40A and touch panel 42A. For example, the KB 31 is used in selecting the mode of operation of the ultrasonic diagnostic apparatus.

The trackball 32 and mouse 33 are mainly used as pointing (selecting) means for conducting selection of an item displayed on the CRT device 30A. For example, the trackball 32 is used in selecting a point displayed on the CRT device 30A, and the mouse 33 is used in verifying items displayed on the CRT device 30A.

Now the operation of the ultrasonic diagnostic apparatus 100A will be generally described.

After the ultrasonic diagnostic apparatus 100A has been activated and the operator has designated several operation conditions, the transmitting/receiving means 2 drives the ultrasonic probe 1 to emit ultrasound from the ultrasonic probe 1 toward the subject. The ultrasonic probe 1 is grabbed by the operator and is abutted against a predefined portion of the subject. The ultrasonic probe 1 detects ultrasound reflected from the subject, converts the ultrasound into corresponding electric signals, and outputs the signals to the transmitting/receiving means 2. The transmitting/receiving means 2 receives the electric signals detected by the ultrasonic probe 1 and sends them to the signal processing means 3.

The signal processing means 3 conducts signal processing including amplification, filtering and the like on the signals received from the transmitting/receiving means 2, and sends the processed signals to the cine memory 51 in the ultrasonic signal processing means 50.

The cine memory 51 is a memory that can store a plurality of ultrasonic images, and stores the ultrasonic receive signals supplied from the signal processing means 3 in order of data input for every ultrasonic image in time order.

The digital scan converter (DSC) 52 reads ultrasonic image data from the cine memory 51 in response to a control command from the first control means 54, and outputs the data to the image processing means 53.

The image processing means 53 conducts processing for displaying image data output by the DSC 52 and status data read out from the status table 55 on the CRT device 30A following the control command from the first control means 54.

The status table 55 stores information indicating the output status, for example, output completed, output in progress, or output waiting, of the ultrasonic image data in the cine memory 51.

FIG. 10 shows an exemplary screen displayed on the CRT device 30A.

In FIG. 10, a display screen 200 of the CRT device 30A is comprised of an image display region 202 in which a result of scanning by the ultrasonic probe 1 is displayed as an image, an output status message display region 204, and a cine gauge display region 206.

The output status message display region 204 displays the output status, for example, "Output completed", "Output in progress" or "Output waiting".

The cine gauge display region 206 displays a status among "Output completed", "Output in progress" and "Output waiting" with respect to an image read out from the cine memory 51.

While the CRT device 30A displays ultrasonic images, the LCD device 40A and touch panel 42A serve as interactive means for the operation of the ultrasonic diagnostic apparatus 100A.

FIG. 11 exemplarily shows items displayed on the LCD device 40A as graphics and messages from the graphic processing means 58 under a control command of the second control means 56, for issuing an operation command to the ultrasonic diagnostic apparatus 100A.

The B-mode Select/Show portion 301 is for indicating that an ultrasonic cross-sectional image produced by scanning the interior of the subject with an ultrasonic beam, obtaining reflection signals, and brightness-modulating the reflection signals on the screen of the CRT device 30 is displayed in the image display region 202 of the CRT device 30A, and for issuing a command to select that mode.

The D-mode Select/Show portion 302 is for indicating that velocity information on blood flow etc. obtained by utilizing the Doppler effect of ultrasound is displayed as an image in the image display region 202 of the CRT device 30A, and for selecting that mode.

The M-mode Select/Show portion 303 is for indicating that the temporal position change of a reflecting source along an ultrasonic beam direction interpreted as a temporal change of reflection waves is displayed in the image display region 202 of the CRT device 30A as a motion curve, and for selecting that mode.

The Single/Dual Select/Show portion 304 is for indicating whether in a state for displaying an image corresponding to one time point (or time span) or for displaying images corresponding to different time points side by side on the screen, and issuing a command for these operations.

The Loop/One-way Select/Show portion 305 is for indicating whether in a state for repeatedly returning the display to the top image displayed after displaying the last cine image or for terminating the display after one-way display of the images in time order, and for issuing a command for these operations.

The Normal/Cine Select/Show portion 306 is for indicating whether the display mode is in a normal display mode or in a cine mode, and for issuing a command for these operations.

The Freeze/Release Select/Show portion 307 is for indicating that image display refresh is temporarily suspended (frozen) during cine display, and image display refresh is resumed by releasing the freeze, and for issuing a command for these operations.

The Rewind Select/Show portion 308 is for selecting an operation of rewinding images in reverse time order while the Rewind Select/Show portion 308 is pressed during freeze, and freeze-displaying the image reached at the time of releasing the Rewind Select/Show portion 308.

The Jog Dial Select/Show portion 309 is for indicating a state in which a plurality of images stored in the cine memory 51 are manually switched in response to "Back" and "Forward" operations of the operator, and for issuing a command for these operations.

The Save Select/Show portion 310 is for indicating that an image displayed at the time of pressing the Save Select/Show portion 310 during freeze is saved, and for issuing a command for this operation.

The Recall Select/Show portion 311 is for indicating that an image saved by pressing the Save Select/Show portion 310 is recalled and displayed, and for issuing a command for this operation.

The Output Select/Show portion 312 is for indicating that data displayed on the CRT device 30A is output to the printer device 60, and for issuing a command for this operation.

The two-dimensional position of a pressed portion in a touch panel 42A is detected by a touch position detection circuit (not shown), and is input to the second control means 56 via the touch sensor interface (I/F) 57. The second control means 56 recalculates the position information detected by the touch position detection circuit into a position in the LCD device 40A, and detects a pressed position corresponding to a Show position on the LCD device 40A.

When the screen exemplarily shown in FIG. 11 is displayed on the LCD device 40A, the operator presses a Show portion on the LCD device 40A via the touch panel 42A over the front surface of the LCD device 40A; then, the pressed portion is detected by the touch position detection circuit, and is input to the second control means 56 via the touch sensor I/F 57. Thus, the second control means 56 can detect that a position corresponding to a Show portion of the LCD device 40A is pressed. Therefore, the use of the touch panel 42A allows the operator to directly press a Show portion of the LCD device 40A through the touch panel 42 with the finger, for example, to conduct a desired operation while viewing the display screen of the LCD device 40A, in a manner similar to the operation of position selection by the keyboard, trackball or mouse.

Since the pressing of the touch panel 42A over the front surface of the LCD device 40A is more direct than position selection using the keyboard, trackball or mouse, the position selection can be done more accurately and the operation is easier. Moreover, the display on the LCD device 40A is easy for the operator to comprehend, thus providing convenience. Furthermore, the number of keyboards can be reduced.

Although the ultrasonic diagnostic apparatus 100A having high interactivity has been provided by using the LCD device 40A provided with the touch panel 42A and the CRT device 30A with their functions separated as described above, there is a need to further improve ease of operation. Typical examples of this need will be described below.

There is a need to obtain a more detailed image by magnifying a certain portion, for example, a heart portion, in an image displayed in the image display region 202 illustrated in FIG. 10 of the CRT device 30A. For example, it would be convenient if such a magnified image could be displayed on the LCD device 40A while displaying an image in the image display region 202 of the CRT device 30A. Such a need has existed.

Moreover, there is a need to measure the size of the heart, for example, in the magnified image.

However, since the conventional LCD device 40A is provided mainly for the purpose of interactive operations, the graphic processing means 58 is not capable of processing for ultrasonic cross-sectional image display or zoom-in display. Thus, the existing LCD device 40A cannot achieve such image display.

If, in the existing apparatus configuration, signals processed by the image processing means 53 that performs display processing for the CRT device 30A could be output to the LCD device 40A and displayed on the LCD device 40A in a way similar to display by the CRT device 30A, only a switch for redirecting the signals output by the image processing means 53 from the CRT device 30A to the LCD device 40A would be needed. However, display data for the LCD device 40A and those for the CRT device 30A are quite different, and therefore, even if the processed signals from the image processing means 53 should be output to the LCD device 40A by redirecting the signals by the switch, the desired image could not be displayed.

To enable the LCD device 40A to conduct such display, means similar to those for allowing the CRT device 30A to conduct display, for example, circuits such as the cine memory 51, DSC 52, and image processing means 53, are needed in addition to the graphic processing means 58, and also the processing functions of the first control means 54 should be added to the second control means 56. However, this complicates the configuration of an ultrasonic diagnostic apparatus, and raises its price.

Moreover, greater flexibility in use mode is desired because two display devices, i.e., the CRT device 30A and LCD device 40A, are available. However, despite the provision of the two display devices, i.e., the CRT device 30A and LCD device 40A, this need cannot be easily met because the two are designed for different purposes.

SUMMARY OF THE INVENTION

It is therefore an object of the present invention is to provide an ultrasonic diagnostic apparatus that can satisfy the aforementioned needs, and improve ease of operation.

An ultrasonic diagnostic apparatus of the present invention comprises, as a basic configuration, arithmetic control/signal processing means for conducting arithmetic control and signal processing for ultrasonic diagnosis, and controlling display processing corresponding to at least first and second display modes; storage means for storing ultrasonic reflection signals detected by an ultrasonic probe; first display means capable of displaying graphics, messages and images; second display means capable of displaying graphics, messages and images; position detecting means for detecting a selected position in a display portion of said second display means; first display processing means for conducting signal processing of the graphics, images and messages displayed on said first display means; and second display processing means for conducting signal processing of the graphics, images and messages displayed on said second display means.

For the first and second display means, a CRT device, a liquid crystal display device or the like, can be arbitrarily combined for use.

The position detecting means is a touch panel, for example.

The pointing means is a keyboard, a trackball, and a mouse, for example.

In accordance with a first aspect of the present invention, in the first display mode, said arithmetic control/signal processing means (a1) drives said first display processing means to display on said first display means "ultrasonic image information and its output status information" based on the ultrasonic reflection signals stored in said storage means, and (a2) drives said second display processing means to display on said second display means "ultrasonic processing, operation, status message/graphic display information" not containing said "ultrasonic image information and its output status information", and conducts task processing for ultrasonic diagnosis in response to an operation detected by said position detecting means; and in the second display mode, said arithmetic control/signal processing means (b1) drives said first display processing means to display on said first display means "ultrasonic processing, operation, status message/graphic display information" not containing said ultrasonic image information and its output status information, and (b2) controls said second display processing means to display on said second display means said "ultrasonic image information and its output status information" based on the ultrasonic reflection signals stored in said storage means, and conducts processing in response to a position detection signal detected by said position detecting means.

In accordance with a second aspect of the present invention, in the first display mode, said arithmetic control/signal processing means (aa1) drives said first display processing means to display on said first display means "ultrasonic image information and its output status information" based on the ultrasonic reflection signals stored in said storage means, and (aa2) drives said second display processing means to display on said second display means "ultrasonic processing, operation, status message/graphic display information" not containing said "ultrasonic image information and its output status information", and conducts task processing for ultrasonic diagnosis in response to an operation detected by said position detecting means; and in the second display mode, said arithmetic control/signal processing means (bb1) drives said first display processing means to display on said first display means "ultrasonic processing, operation, status message/graphic display information" not containing said ultrasonic image information and its output status information, and inputs an operation command corresponding to an operation via pointing means, and (bb2) drives said second display processing means to display on said second display means said "ultrasonic image information and its output status information" stored in said storage means, and conducts processing in response to a position detection signal detected by said position detecting means.

In accordance with a third aspect of the present invention, in the first display mode, said arithmetic control/signal processing means (aa1) drives said first display processing means to display on said first display means "ultrasonic image information and its output status information" based on the ultrasonic reflection signals stored in said storage means, and (aa2) drives said second display processing means to display on said second display means "ultrasonic processing, operation, status message/graphic display information" not containing said "ultrasonic image information and its output status information", and conducts task processing for ultrasonic diagnosis in response to an operation detected by said position detecting means; and in the second display mode, said arithmetic control/signal processing means (aa1) drives said first display processing means to display on said first display means said "ultrasonic image information and its output status information" based on the ultrasonic reflection signals stored in said storage means, and (aa3) drives said second display processing means to display on part of said second display means said "ultrasonic processing, operation, status message/graphic display information" not containing said "ultrasonic image information and its output status information", and to display on another part of said second display means information identical or similar to said "ultrasonic image information and its output status information" displayed on said first display means, and conducts processing according to a position selection on said displayed image detected by said position detecting means.

Preferably, the processing in response to a position detecting signal detected by said position detecting means is zoom processing.

Preferably, the processing in response to a position detecting signal detected by said position detecting means is measurement processing.

According to the present invention, several use modes desired in an ultrasonic diagnostic apparatus can be implemented while improving ease of operation by effectively using two display devices.

Further objects and advantages of the present invention will be apparent from the following description of the preferred embodiments of the invention as illustrated in the accompanying drawings.

BRIEF DESCRIPTION OF THE DRAWINGS

FIG. 2 is an exterior view of the ultrasonic diagnostic apparatus illustrated in FIG. 1.

DETAILED DESCRIPTION OF THE INVENTION

Preferred embodiments of the ultrasonic diagnostic apparatus in accordance with the present invention will be described below with reference to the accompanying drawings.

First Embodiment

Figure 1:
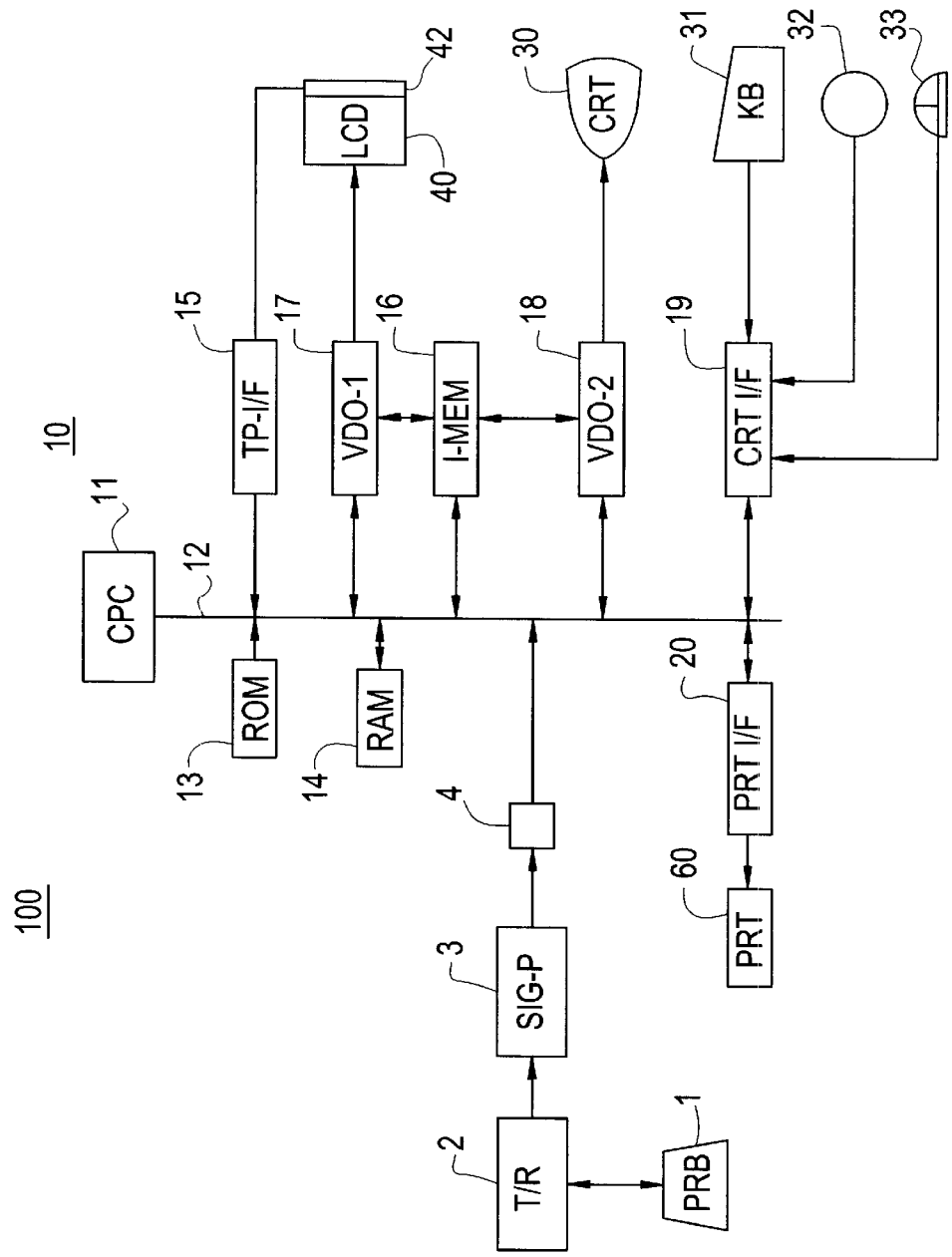
FIG. 1 is a configuration diagram of a first embodiment of an ultrasonic diagnostic apparatus of the present invention.

FIG. 1 is a configuration diagram of an ultrasonic diagnostic apparatus in accordance with an embodiment of the present invention.

The ultrasonic diagnostic apparatus 100 illustrated in FIG. 1 comprises an ultrasonic probe (search unit) 1, transmitting/receiving means 2, signal processing means 3, and an ultrasonic sensor interface (I/F) 4.

The ultrasonic diagnostic apparatus 100 further comprises ultrasonic signal processing means 10, a CRT device 30, a keyboard (KB) 31, a liquid crystal display (LCD) device 40, a touch panel 42, and a printer device 60.

The ultrasonic diagnostic apparatus 100 further comprises a trackball 32 and a mouse 33. The trackball 32 and mouse 33, however, are not essential, and they can be omitted. It should be noted that the following description is directed to a case in which the trackball 32 and mouse 33 are present.

The ultrasonic signal processing means 10 comprises arithmetic control/signal processing means 11, a bus 12, an ROM 13, an RAM 14, a touch sensor interface (I/F) 15, an image memory 16, first video signal processing means 17, second video signal processing means 18, a CRT interface (I/F) 19, and a printer (PRT) interface 20.

The arithmetic control/signal processing means 11 is connected via the bus 12 to the ROM 13, RAM 14, touch sensor I/F 15, image memory 16, first video signal processing means 17, second video signal processing means 18, CRT I/F 19, and printer I/F 20.

The ultrasonic probe 1, transmitting/receiving means 2 and signal processing means 3 are the same as those in the prior art described with reference to FIG. 9. It should be noted that the ultrasonic sensor I/F 4 is added for inputting signals output by the signal processing means 3 to the ultrasonic signal processing means 10 in this embodiment.

The CRT device 30 corresponds to the first display means of the present invention, and the LCD device 40 corresponds to the second display means of the present invention.

In the present invention, the same type of display devices may be used for the first and second display means; for example, the CRT devices may be used for the first and second display means. Alternatively, the LCD devices may be used for the first and second display means. Conversely to the first embodiment, it is possible to use the LCD device as the first display means and the CRT device as the second display means.

It should be noted that the first embodiment describes a case in which the CRT device 30 is employed for the first display means, and the LCD device 40 is employed for the second display means.

Figure 9:
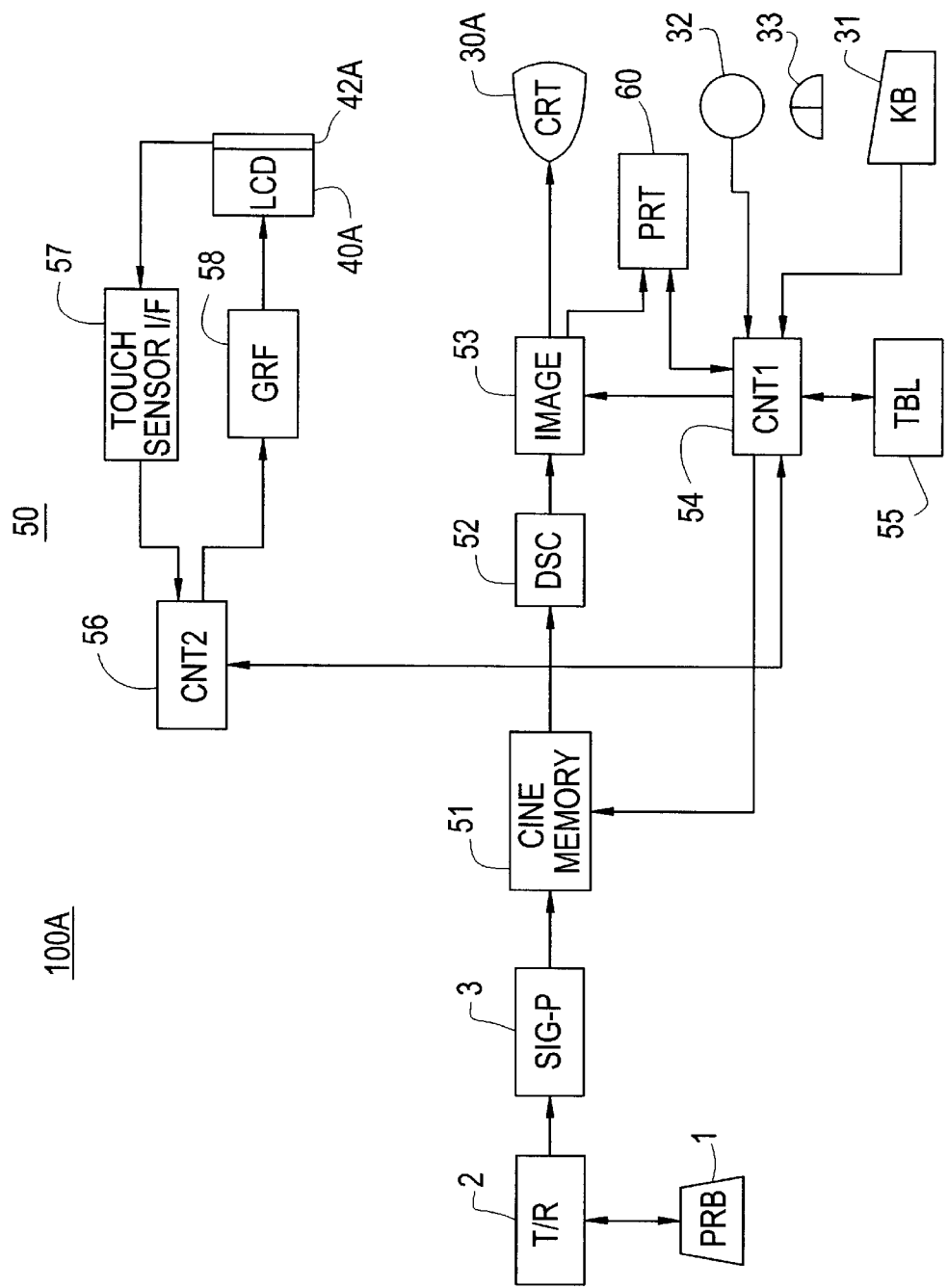
FIG. 9 is a configuration diagram of a conventional ultrasonic diagnostic apparatus.

The CRT device 30 and LCD device 40 correspond to the CRT device 30A and LCD device 40A illustrated in FIG. 9, and they functionally resemble the CRT device 30A and LCD device 40A illustrated in FIG. 9. However, in the present invention, items displayed on the CRT device 30 and LCD device 40 sometimes differ from those displayed on the CRT device 30A and LCD device 40A illustrated in FIG. 9, as will be described below. Although the touch panel 42 illustrated in FIG. 1 is the same as the touch panel 42A illustrated in FIG. 9 in principle, the use thereof is different between the present embodiment and the conventional case.

In the first embodiment of the present invention, since the LCD device 40, unlike the conventional LCD device 40A, displays images such as ultrasonic cross-sectional images similar to those on the CRT device 30, the LCD device 40 used is functionally provided with a capability of displaying images such as ultrasonic cross-sectional images in addition to graphics and messages, and has a display area of a size that allows display of images such as ultrasonic cross-sectional images.

In the first embodiment of the present invention, since the CRT device 30, unlike the conventional CRT device 30A, may display graphics and interactive messages displayed on the LCD device 40A described with reference to FIG. 9 in addition to the images such as ultrasonic cross-sectional images displayed on the CRT device 30A described with reference to FIG. 9, a CRT device capable of displaying graphics, messages and the like in addition to displaying images is used for the CRT device 30.

The first video signal processing means 17 corresponds to the first display processing means of the present invention, and the second video signal processing means 18 corresponds to the second display processing means of the present invention.

In the first embodiment, since quite different types of display means, such as the LCD device 40 and the CRT device 30, are employed, a first interface circuit (not shown) between the first video signal processing means 17 and LCD device 40 is different from a second interface circuit (not shown) between the second video signal processing means 18 and CRT device 30; but the processing functions of the first and second video signal processing means 17 and 18 are the same. Such processing functions include a display processing function for images such as ultrasonic images, processing of several types of graphics, and a processing function for messages including characters and numbers.

It should be noted that, when the first and second display means are the same type of display devices, for example, LCD devices, the aforesaid interface circuits are the same, as of course are the first and second signal processing means 17 and 18.

By contrast with the prior art described with reference to FIG. 9, the graphic processing means 58 for conducting display processing for the LCD device 40A illustrated in FIG. 9 has a graphic and message processing function and no ultrasonic image or other such image processing function; on the other hand, the first video signal processing means 17 illustrated in FIG. 1 has functions similar to those of the graphic processing means 58, and in addition, a processing function for images such as ultrasonic cross-sectional images. Moreover, the image processing means 53 configured as a dedicated circuit for conducting display processing for the CRT device 30A illustrated in FIG. 9 has functions of ultrasonic cross-sectional image processing for the image display region 202 illustrated in FIG. 10, graphics and message processing for the output status message display region 204, and graphics and message processing for the cine gauge display region 206; on the other hand, the second video signal processing means 18 illustrated in FIG. 1 has processing functions similar to those of the graphic processing means 58 in addition to these functions.

The first video signal processing means 17 and the second video signal processing means 18 are constituted using digital signal processors (DSP's), for example. The DSP is a means that processes signals at high speed; and if the first and second video signal processing means 17 and 18 are constituting using DSP's, several types of desired processing can be implemented by programs, and modification of the processing is easy.

Figure 2A:
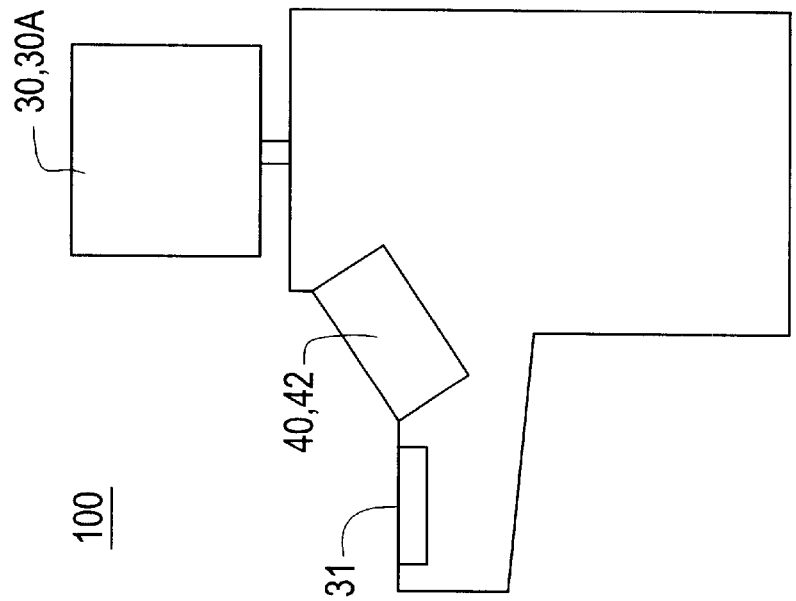
FIG. 2(A) is a front elevational view.
Figure 2B:
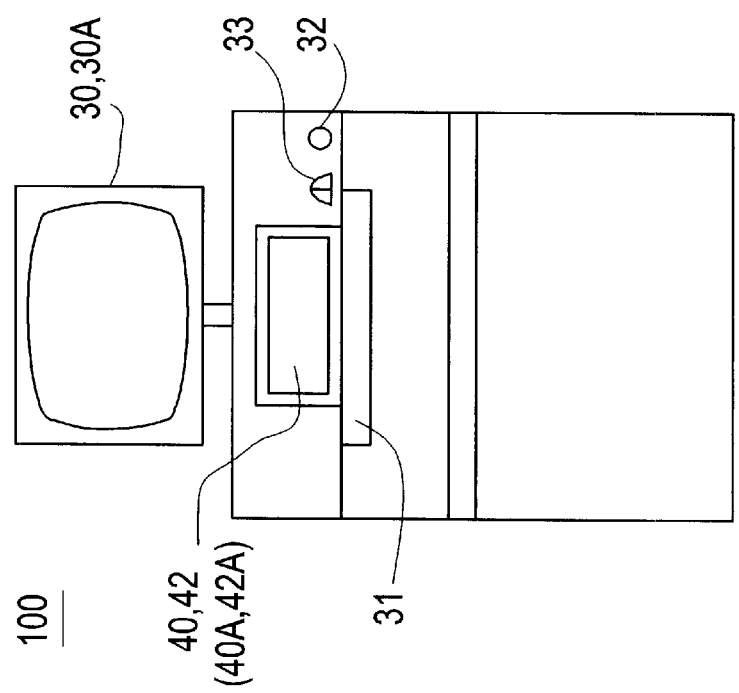
FIG. 2(B) is a side view.

The CRT device 30, LCD device 40, keyboard (KB) 31, trackball 32, and mouse 33 are disposed as illustrated in FIGS. 2(A) and (B), as in the prior art.

The CRT device 30 is disposed at a position to allow a physician or an examination technician (referred to as an operator hereinbelow) who sits down in front of the operation panel of the ultrasonic diagnostic apparatus 100 and operates the ultrasonic probe 1 on a subject to easily view the CRT device 30, for example, at a position above the operation panel of the ultrasonic diagnostic apparatus.

The LCD device 40 is disposed within arm's reach of the operator on the operation panel of the ultrasonic diagnostic apparatus below the CRT device 30, to allow the operator who sits down in front of the operation panel of the ultrasonic diagnostic apparatus 100 and operates the ultrasonic probe 1 on the subject to view displayed items, and to issue operation commands to the ultrasonic diagnostic apparatus via the touch panel 42 provided over the front surface of the display portion of the LCD device 40.

The touch panel 42 is made of a transparent piezoelectric sheet, and is adhered to the front surface of the display screen of the LCD device 40. The touch panel 42 is connected with a position detection circuit (not shown), and an output from the position detection circuit is input to the arithmetic control/signal processing means 11 via the touch sensor I/F 15.

The operator can view items displayed on the display screen of the LCD device 40 through the transparent touch panel 42. Moreover, after verifying the displayed items, if the operator presses a certain display portion with the finger or an object having a sharp tip to issue an operation command for the ultrasonic diagnostic apparatus, a voltage is generated at a pressed position in the touch panel 42. The position detection circuit detects the pressed position in a two-dimensional manner, and inputs the detected position to the arithmetic control/signal processing means 11 via the touch sensor I/F 15. The arithmetic control/signal processing means 11 detects what portion of the display screen of the LCD device 40 the position information corresponds to, and identifies an operation command related to an item displayed on the LCD device 40.

In this manner, the LCD device 40 and touch panel 42 are used for direct interactive means between the operator and the ultrasonic diagnostic apparatus for the operation of the ultrasonic diagnostic apparatus.

The CRT I/F 19 is supplied with signals from the KB 31, trackball 32 and mouse 33, and outputs the signals to the arithmetic control/signal processing means 11 via the bus 12.

The KB 31 is used in, for example, selecting the mode of operation of the ultrasonic diagnostic apparatus.

The trackball 32 and mouse 33 are placed beside the KB 31 because they are mainly used as pointing (interactive) means for the items displayed on the CRT device 30. For example, the trackball 32 is used for selecting a portion displayed on the CRT device 30, and the mouse 33 is used for verifying the particulars of items displayed on the CRT device 30.

The printer I/F 20 is an interface circuit for conducting image output and message output from the arithmetic control/signal processing means 11 to the printer device 60.

Although the ultrasonic signal processing means 10 illustrated in FIG. 1 does not have the cine memory 51 and digital scan converter (DSC) 52 described with reference to FIG. 9, an operation identical to that of the cine memory 51 and DSC 52 is achieved by operating the image memory 16 under control of the arithmetic control/signal processing means 11. Therefore, processing similar to that by the cine memory 51 and DSC 52 in the existing ultrasonic diagnostic apparatus is implemented in this embodiment of the present invention, and such an operation is called a "cine operation" also in this embodiment. The image memory 16 is connected to the first video signal processing means 17 and the second video signal processing means 18 via the bus, and supplies image data similar to those from the cine memory 51 to both the first and second video signal processing means 17 and 18.

Although the ultrasonic signal processing means 10 illustrated in FIG. 1 does not have the status table 55 described with reference to FIG. 9, processing similar to that by the status table 55 is achieved by the RAM 14 operating under control of the arithmetic control/signal processing means 11.

The arithmetic control/signal processing means 11 is implemented by a computer, for example, and conducts the processing described above and below in accordance with several programs stored in the ROM 13.

Display Modes

In the first embodiment of the present invention, two display modes as exemplarily shown in Table 1 below are defined. The substance of the modes is stored in the ROM 13.

TABLE 1

Figure 3:
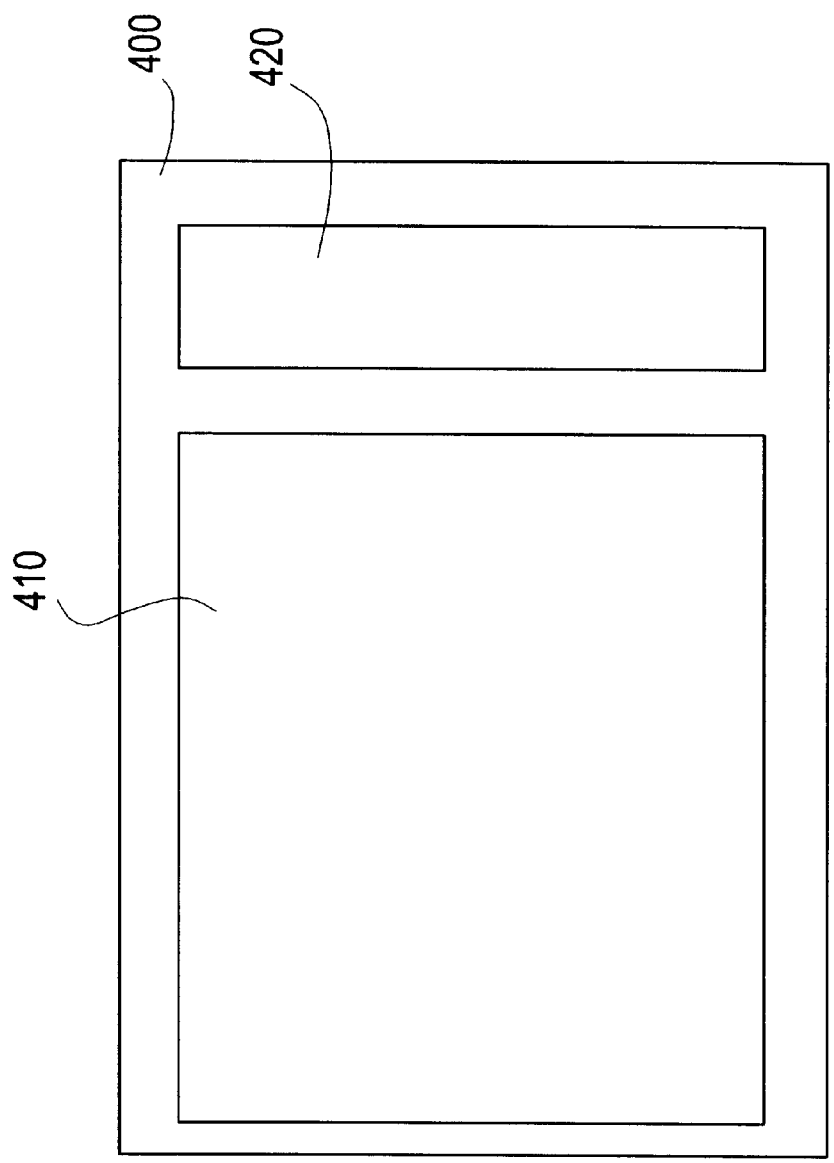
FIG. 3 shows a first exemplary screen displayed on a liquid crystal display device illustrated in FIGS. 1 and 2.
Figure 10:
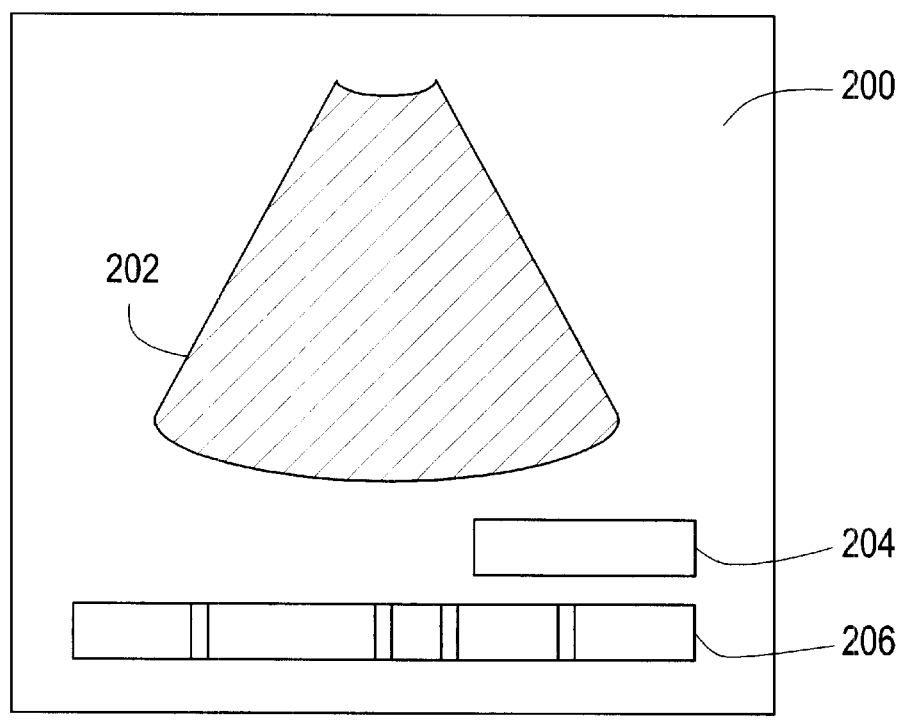
FIG. 10 shows exemplary display of an ultrasonic image.

|  | First Display Mode | Second Display Mode |
| --- | --- | --- |
| CRT device | Display illustrated in FIG. 10 | Display illustrated in FIG. 3 |
| LCD device | Display illustrated in FIG. 3 | Display illustrated in FIG. 10 |

The first display mode is a display mode in which the screen illustrated in FIG. 10 is displayed on the CRT device 30, and the screen relating to the operation of the ultrasonic diagnostic apparatus 100 exemplarily shown in FIG. 3 is displayed on the LCD device 40.

The second display mode is, conversely to the first display mode, a display mode in which the screen illustrated in FIG. 10 is displayed on the LCD device 40, and the screen relating to the operation of the ultrasonic diagnostic apparatus 100 exemplarily shown in FIG. 3 is displayed on the CRT device 30.

Displayed Items in FIG. 10

The displayed items illustrated in FIG. 10 will now be described. The displayed items illustrated in FIG. 10 are basically the same as those in the conventional case described with reference to FIG. 9, except that, in the embodiment of the present invention, the display illustrated in FIG. 10 can be displayed on the LCD device 40, as well as on the CRT device 30.

The display screen 200 in FIG. 10 is comprised of an image display region 202 in which an ultrasonic cross-sectional image that is a result of scanning by the ultrasonic probe 1 and is stored in the image memory 16 that operates similarly to the cine memory 51 is displayed, an output status message display region 204, and a cine gauge display region 206.

The output status message display region 204 displays the output status, for example, "Output completed", "Output in progress" or "Output waiting", with respect to an image read out from the RAM 14 that operates similarly to the status table 55.

The cine gauge display region 206 displays a status of "Output completed", "Output in progress" or "Output waiting" with respect to an image read out from the image memory 16 that operates similarly to the cine memory 51.

Display Items in FIG. 3

The displayed items illustrated in FIG. 3 will now be described.

In the display illustrated in FIG. 3, a display screen 400 is divided into an items display region 410 and an operation-related display region 420.

The items display region 410 displays several types of messages and graphics relating to the processing, operation and status of the ultrasonic diagnostic apparatus 100, and messages and graphics relating to operation results.

Figure 11:
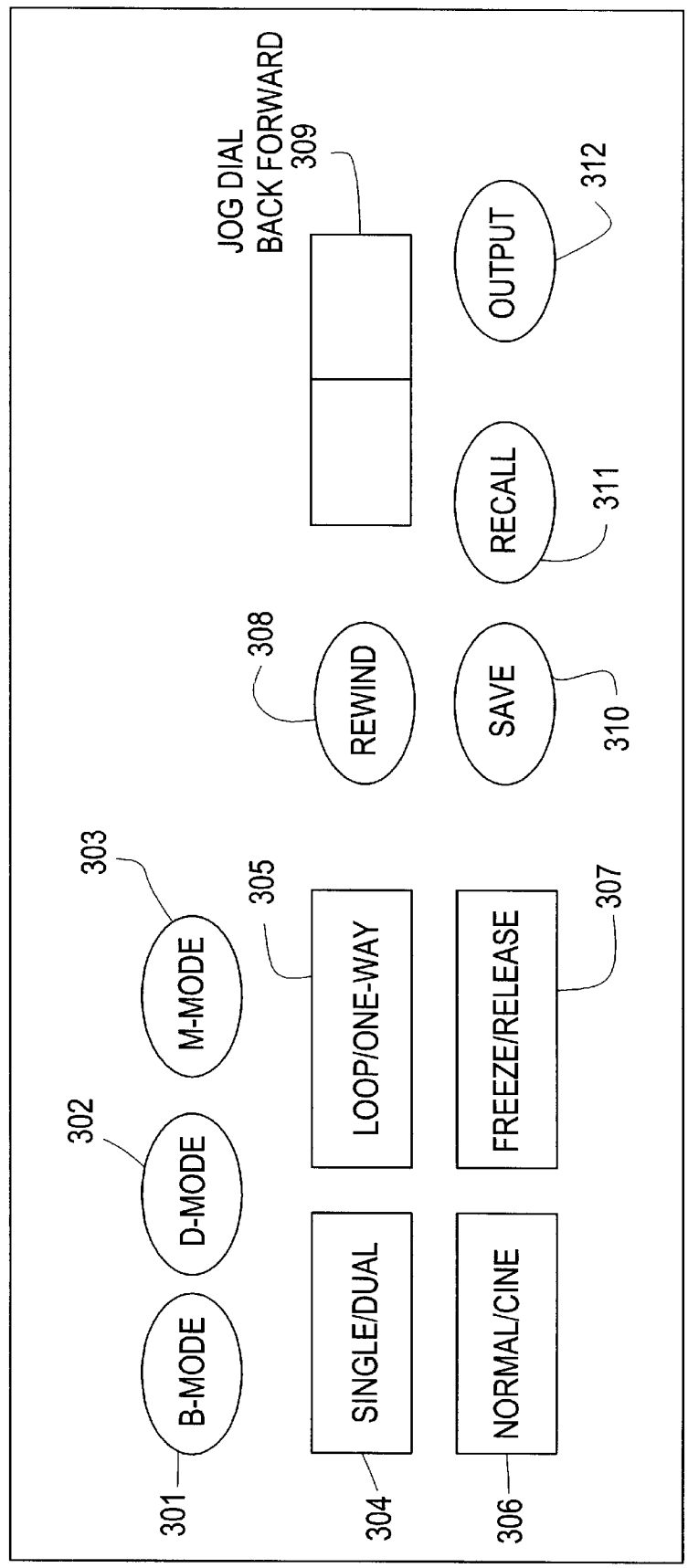
FIG. 11 shows exemplary display of operation items of the ultrasonic diagnostic apparatus.

While the operation-related display region 420 displays items similar to the display described with reference to FIG. 11, the arrangement is different, and displayed items not included in FIG. 11 are added.

In the present invention, the displayed items illustrated in FIG. 10 will be referred to as "ultrasonic image information and its output status information". On the other hand, the displayed items in the present invention illustrated in FIGS. 3 and 4 will be referred to as "ultrasonic processing, operation, status message/graphic display information not containing the ultrasonic image information".

Figure 4:
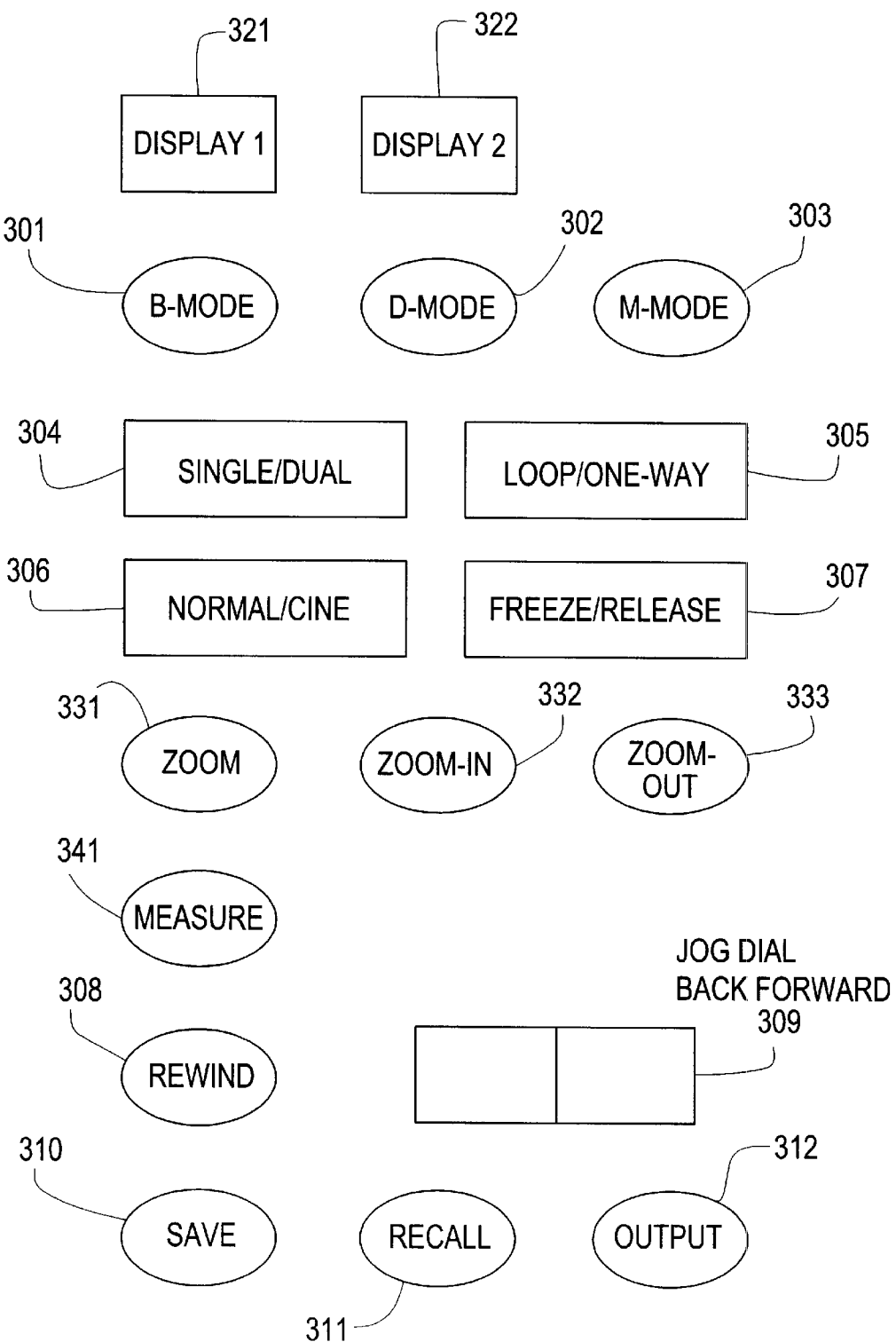
FIG. 4 is a first partial enlarged view of a screen displayed on the liquid crystal display device illustrated in FIG. 3.

Exemplary displayed items in the operation-related display region 420 are illustrated in FIG. 4.

The display example illustrated in FIG. 4 has an arrangement similar to but different from the display example illustrated in FIG. 11 as described above; and there are added a First Display Mode Select/Show portion 321, a Second Display Mode Select/Show portion 322, a Zoom Processing-related Select/Show portions 331–333, and a Measurement Select/Show portion 341.

The First Display Mode Select/Show portion 321 and Second Display Mode Select/Show portion 322 are for selecting one of the aforementioned first and second display modes, and for indicating the selected display mode in, for example, red and the unselected display mode in, for example, green.

In the present embodiment, since the touch panel 42 is adhered to the front surface of the display screen of the LCD device 40, when the items shown in FIG. 3 are displayed on the LCD device 40 and the operator presses the First Display Mode Select/Show portion 321 or the Second Display Mode Select/Show portion 322 with the finger, the selection is effected accordingly. On the other hand, when the items shown in FIG. 3 are displayed on the CRT device 30, the display mode is selected by, for example, using the mouse 33 or KB 31.

The Zoom Processing-related Select/Show portions 331–333 are comprised of a Zoom Select/Show portion 331, a Zoom-in Display Select/Show portion 332, and Zoom-out Select/Show portion 333, and they are used in zooming in and zooming out a predefined portion in an ultrasonic cross-sectional image. Details of the operation will be described later with reference to examples.

The Measurement Select/Show portion 341 is used in measuring the size of a certain portion, for example, the kidney, in an ultrasonic cross-sectional image. Details of the operation will be described later with reference to examples.

Although the other parts are basically similar to those described with reference to FIG. 11, they will be briefly described in below.

The B-mode Select/Show portion 301 is for indicating that an ultrasonic cross-sectional image produced by scanning the interior of the subject with an ultrasonic beam, obtaining reflection signals, and brightness-modulating the reflection signals on the screen of the CRT device 30 or LCD device 40 (which will be generically referred to as a display device hereinbelow) is displayed in the image display region 202 of the display device, and for issuing a command to select that mode.

The D-mode Select/Show portion 302 is for indicating that velocity information on blood flow etc. obtained by utilizing the Doppler effect of ultrasound is displayed as an image in the image display region 202 of the display device, and for selecting that mode.

The M-mode Select/Show portion 303 is for indicating that the temporal position change of a reflecting source along an ultrasonic beam direction interpreted as a temporal change of reflection waves is displayed in the image display region 202 of the display device as a motion curve, and for selecting that mode.

The Single/Dual Select/Show portion 304 is for indicating whether in a state for displaying an image corresponding to one time point (or time span) or for displaying images corresponding to different time points side by side on the screen, and issuing a command for these operations.

The Loop/One-way Select/Show portion 305 is for indicating whether in a state for repeatedly returning the display to the top image displayed after displaying the last cine image or for terminating the display after one-way display of the images in time order, and for issuing a command for these operations.

The Normal/Cine Select/Show portion 306 is for indicating whether the display mode is in a normal display mode or in a cine mode, and for issuing a command for these operations.

The Freeze/Release Select/Show portion 307 is for indicating that image display refresh is temporarily suspended (frozen) during cine display, and image display refresh is resumed by releasing the freeze, and for issuing a command for these operations.

The Rewind Select/Show portion 308 is for selecting an operation of rewinding images in reverse time order while the Rewind Select/Show portion 308 is pressed during freeze, and freeze-displaying an image reached at a time of releasing the Rewind Select/Show portion 308.

The Jog-Dial Select/Show portion 309 is for indicating a state in which a plurality of images stored in the cine memory 51 are manually switched in response to "Back" and "Forward" operations of the operator, and for issuing a command for these operations.

The Save Select/Show portion 310 is for indicating that an image displayed at the time of pressing the Save Select/Show portion 310 during freeze is saved, and for issuing a command for this operation.

The Recall Select/Show portion 311 is for indicating that an image saved by pressing the Save Select/Show portion 310 is recalled and displayed, and for issuing a command for this operation.

The Output Select/Show portion 312 is for indicating that data displayed on the display device is output to the printer device 60 via the printer I/F 20, and for issuing a command for this operation.

Explanation of Operation of Ultrasonic Diagnostic Apparatus 100

(1) Activation: When the ultrasonic diagnostic apparatus 100 is activated, the arithmetic control/signal processing means 11 automatically selects the display mode 1 as an initial state, and stores the display mode in the RAM 14.

On the LCD device 40, the screens exemplarily shown in FIGS. 3 and 4 are displayed. To this end, the arithmetic control/signal processing means 11 directs the first video signal processing means 17 to display the screens illustrated in FIGS. 3 and 4 on the LCD device 40, and the second video signal processing means 18 to display the screen illustrated in FIG. 10 on the CRT device 30. The first video signal processing means 17 sends display information to the LCD device 40 so that the screens exemplarily shown in FIGS. 3 and 4 are displayed. The second video signal processing means 18 sends display information to the CRT device 30 so that the screen exemplarily shown in FIG. 10 is displayed.

(2) Designation of Operating Conditions: The operator views the items displayed on the LCD device 40 and designates the operation conditions of the ultrasonic diagnostic apparatus 100. An example of the designation process will be now described. If the operator desires to change the display mode, the operator uses a finger to press the Second Display Select/Show portion 322 illustrated in FIG. 4 in the operation-related display region 420 in the second display screen 400 of FIG. 3 displayed on the LCD device 40.

In response to this operation, the position detection circuit (not shown) detects the piezoelectric state of the touch panel 42, and outputs the state to the arithmetic control/signal processing means 11 via the touch sensor I/F 15. The arithmetic control/signal processing means 11 detects that the Second Display Mode Select/Show portion 322 is pressed.

The arithmetic control/signal processing means 11 drives the first video signal processing means 17 to change the display color of the First Display Mode Select/Show portion 321 from, for example, red to green, and the display color of the Second Display Mode Select/Show portion 322 from green to red. Thus, the operator knows that the change of display mode is effected as designated.

After a predefined time for the operator to verify the operation, the arithmetic control/signal processing means 11 directs the first video signal processing means 17 to display the screen illustrated in FIG. 10 on the LCD device 40, and the second video signal processing means 18 to display the screen illustrated in FIG. 3 on the CRT device 30. The first video signal processing means 17 sends display information to the LCD device 40 so that the screen exemplarily shown in FIG. 10 is displayed. The second video signal processing means 18 sends display information to the CRT device 30 so that the screen exemplarily shown in FIG. 3 is displayed.

Thereafter, operations using the CRT device 30 are done with, for example, the KB 31, trackball 32 or mouse 33. For example, when the B-mode Select/Show portion 301 is to be selected, the operator moves a cursor of the mouse 33 to the B-mode Select/Show portion 301 on the CRT device 30 and clicks the mouse, or operates keys using the KB 31 so that the B-mode Select/Show portion 301 is selected. Such an operation is detected by the CRT processing means 19, and is input to the arithmetic control/signal processing means 11 via the bus 12. The arithmetic control/signal processing means 11 thus detects the selection of the B-mode Select/Show portion 301, and stores the mode in the RAM 14. Thereafter, the arithmetic control/signal processing means 11 operates in the B mode.

Similarly, when the Single/Dual Select/Show portion 304 and the Normal/Cine Select/Show portion 306 displayed on the CRT device 30 are selected, for example, Single arid Normal are designated.

After establishing the operation conditions as described above, the operator puts the ultrasonic probe 1 against a predefined portion in the subject. The transmitting/receiving means 2 then drives the ultrasonic probe 1 to illuminate the predefined portion in the subject with ultrasound, and its reflected ultrasound is detected by the ultrasonic probe 1 and is subjected to signal processing such as amplification at the signal processing means 3. The result of the signal processing is supplied to the arithmetic control/signal processing means 11 from the bus 12 via the ultrasonic sensor I/F 4, and is stored in the image memory 16 that functions similarly to the cine memory 51 in FIG. 9.

The first video signal processing means 17 reads out an ultrasonic cross-sectional image stored in the image memory 16, and displays it in the image display region 202 illustrated in FIG. 10 on the LCD device 40. The ultrasonic cross-sectional image varies according to the result of scanning by the ultrasonic probe 1.

Moreover, the first video signal processing means 17 reads out particularities corresponding to the status table 55 stored in the RAM 14, and conducts display in the output status message display region 204 and cine gauge display region 206 on the LCD device 40.

Zoom Processing

A case in which zooming processing is selected will be described hereinbelow with reference to the flow chart in FIG. 5.

Step 1: Zoom Start Selection

In this condition, when the operator desires to view a certain portion displayed in the image display region 202 on the LCD device 40 with magnification, for example, he/she selects the Zoom Select/Show portion 331 illustrated in FIG. 4 displayed on the CRT device 30 using the KB 31 or mouse 33. The CRT processing means 19 inputs this information to the arithmetic control/signal processing means 11. The arithmetic control/signal processing means 11 detects issuance of a zoom start command.

Steps 2 and 3: Zoom Center Position Selection

The operator then uses a finger to press the touch panel 42 at a portion of an ultrasonic cross-sectional image displayed in the image display region 202 on the LCD device 40 which he/she desires to view with magnification. The ultrasonic signal processing means 10 waits until the touch panel 42 is pressed. When the touch panel 42 is pressed, the operation is detected by the position detecting means, and is input to the arithmetic control/signal processing means 11 via the touch sensor interface (I/F) 15. The arithmetic control/signal processing means 11 directs the first video signal processing means 17 to display a predefined area surrounding the selected position with magnification. The first video signal processing means 17 then indicates the selected position by, for example, a red cross mark (x). This display allows the operator to verify the position he/she selected.

Steps 4 and 5: Zoom-in Selection

The operator selects the Zoom-in Display Select/Show portion 332 illustrated in FIG. 4 displayed on the CRT device 30 using the KB 31 or mouse 33. The CRT processing means 19 inputs this information to the arithmetic control/signal processing means 11. The arithmetic control/signal processing means 11 notifies the first video signal processing means 17 of issuance of the "Zoom-in" command. The first video signal processing means 17 displays a certain section centered on the red cross mark of an image read out from the image memory 16 as magnified by a certain factor, for example, by two. The factor may be displayed near the image display region 202.

If the operator desires to further zoom in the image, the operation of Step 4 is repeated. As a result, the image that has currently been magnified is further magnified by a specified factor.

When the image has been magnified as desired by the operator, the operator selects the Output Select/Show portion 312; then, the arithmetic control/signal processing means 11 operates the printer device 60 via the printer I/F 20 to output the image.

Steps 6 and 7: Zoom-out Selection

If the operator feels the magnified image is excessively magnified, the magnified image can be reduced by a specified zoom-out factor, for example, by ½. At this time, the operator selects the Zoom-out Select/Show portion 333 illustrated in FIG. 4 displayed on the CRT device 30 by the KB 31 or mouse 33.

The CRT processing means 19 inputs this information to the arithmetic control/signal processing means 11. The arithmetic control/signal processing means 11 notifies the first video signal processing means 17 of issuance of the "Zoom-out" command. The first video signal processing means 17 displays the certain section centered on the red cross mark of the image read out from the image memory 16 as reduced by a certain zoom-out factor. The factor may be displayed near the image display region 202.

When the image has been reduced as desired by the operator, the operator can select the Output Select/Show portion 312 to output the image to the printer device 60.

Steps 8 and 9: Zoom Termination

When desiring to terminate the zoom processing, the operator selects the Zoom Select/Show portion 331 illustrated in FIG. 4 displayed on the CRT device 30 using the KB 31 or mouse 33. The CRT processing means 19 inputs this information to the arithmetic control/signal processing means 11. Upon detecting this second operation of the Zoom Select/Show portion 331, the arithmetic control/signal processing means 11 terminates the zoom processing. Specifically, the arithmetic control/signal processing means 11 directs the first video signal processing means 17 to terminate the zoom processing. The first video signal processing means 17 restores the display of the image display region 202 of the LCD device 40 to normal display of an ultrasonic cross-sectional image involving no zooming.

As described above, direct pressing of the touch panel 42 at a certain portion displayed in the image display region 202 of the LCD device 40 with the operator's finger enables a predefined range centered on the pressed position to be displayed with zoom-in or zoom-out. Especially, since a desired position in an image displayed in the image display region 202 can be selected by directly pressing the position with the finger, the operation is intuitive and ease of operation is improved.

To achieve more accurate position selection at Step 2, a pen having a sharp tip, for example, may be used in place of the operator's finger. However, the means is not limited to the finger or pen but may be any member or means that can give rise to a piezoelectric phenomenon by pressing the touch panel 42.

Measurement Processing

A case in which measurement is selected will be described hereinbelow with reference to the flow chart in FIG. 6. In this example, a case in which measurement processing is performed on a frozen ultrasonic cross-sectional image magnified by a specified factor at Steps 4 and 5 in FIG. 5 will be explained.

Steps 11 and 12: Measurement Start

When the operator desires to measure the size, distance or the like of a certain portion displayed with magnification in the image display region 202 in the LCD device 40, he/she selects the Measurement Select/Show portion 341 illustrated in FIG. 4 displayed on the CRT device 30 using the KB 31 or mouse 33. The CRT processing means 19 inputs this information to the arithmetic control/signal processing means 11. The arithmetic control/signal processing means 11 detects issuance of the measurement command; forcibly changes the mode into the freeze mode; and notifies the first video signal processing means 17 of the commands.

The first video signal processing means 17 stops the refreshing of the display of the ultrasonic cross-sectional image displayed with magnification in the image display region 202 of the LCD device 40 (freeze display).

In this example, freeze display is automatically activated because more accurate measurement may be made with the ultrasonic cross-sectional image stopped in the measurement mode, and measurement may be automatically enabled without operating the Freeze/Release Select/Show portion 307, thus simplifying operation.

Steps 13 and 14: First Position Selection

After verifying that the ultrasonic cross-sectional image displayed in the image display region 202 of the LCD device 40 has been frozen, the operator selects a first position to be measured. The position selection is performed in a manner similar to the aforementioned zoom center position selection. That is, the operator uses a finger to press the touch panel 42 at a portion of the ultrasonic cross-sectional image freeze-displayed in the image display region 202 of the LCD device 40 that corresponds to a measurement start point. The arithmetic control/signal processing means 11 waits until the touch panel 42 is pressed. When the touch panel 42 is pressed, the operation is detected by the position detecting means, and is input to the arithmetic control/signal processing means 11 via the touch sensor I/F 15. The arithmetic control/signal processing means 11 notifies the first video signal processing means 17 to display the selected position.

Step 15: First Position Display

The first video signal processing means 17 displays the selected measurement start point by, for example, a red cross mark (x). This display allows the operator to verify the position he/she selected.

Steps 16 and 17: Second Position Selection

The operator uses a finger to press the touch panel 42 at a portion of the ultrasonic cross-sectional image freeze-displayed in the image display region 202 of the LCD device 40 that corresponds to a measurement end point. The arithmetic control/signal processing means 11 waits until the touch panel 42 is pressed. When the touch panel 42 is pressed, the operation is detected by the position detecting means, and is input to the arithmetic control/signal processing means 11 via the touch sensor I/F 15. The arithmetic control/signal processing means 11 notifies the first video signal processing means 17 to display the selected position.

Step 18: Mark Display, Distance Calculation, and Output

The first video signal processing means 17 displays the selected measurement end position by, for example, a green cross mark (x). This display allows the operator to verify the position he/she selected.

The arithmetic control/signal processing means 11 measures the distance between the start position and end position from the image data stored in the image memory 16.

Upon completion of the distance measurement, the arithmetic control/signal processing means 11 sends the result to the first video signal processing means 17. The first video signal processing means 17 displays the result near the image display region 202 of the LCD device 40.

If the operator needs to record the result using the printer device 60, he/she operates the Output Select/Show portion 312 to output the result to the printer 60.

Step 19: Termination Operation

After completion of these operations, the arithmetic control/signal processing means 11 releases the freeze state for the termination of the measurement operation. Specifically, the arithmetic control/signal processing means 11 notifies the first video signal processing means 17 of freeze release. The first video signal processing means 17 resumes the refreshing of the image display in the image display region 202 of the LCD device 40.

As described above, the distance between the start position and end position can be measured by directly pressing the touch panel 42 displayed in the image display region 202 of the LCD device 40 at the measurement start position and end position. Especially, since the distance between two desired points of an image freeze-displayed in the image display region 202 is measured by directly pressing the two points with the finger, the distance between two points can be accurately measured.

To achieve more accurate position selection at Steps 13 and 16, a pen having a sharp tip, for example, may be used in place of the operator's finger. However, the means is not limited to the finger or pen but may be any member or means that can give rise to a piezoelectric phenomenon by pressing the touch panel 42.

Although description has been made on a case in which the measurement processing is conducted with an ultrasonic cross-sectional image magnified by a certain factor, the zoom processing and the measurement processing are not necessarily associated, and the measurement processing may be conducted in any operation condition of the ultrasonic diagnostic apparatus 100.

Moreover, although description has been made on a case in which the display is automatically switched to freeze display in the measurement processing, the measurement processing does not need to be associated with the freeze display. That is, the display does not have to be automatically switched to the freeze display in the measurement processing If the switching to the freeze display is required, the Freeze/Release Select/Show portion 307 may be selected at the required time to achieve the freeze display.

Second Embodiment

A second embodiment of the ultrasonic diagnostic apparatus of the present invention will now be described.

Display modes in accordance with the second embodiment are generally shown in Table 2.

TABLE 2

Figure 7:
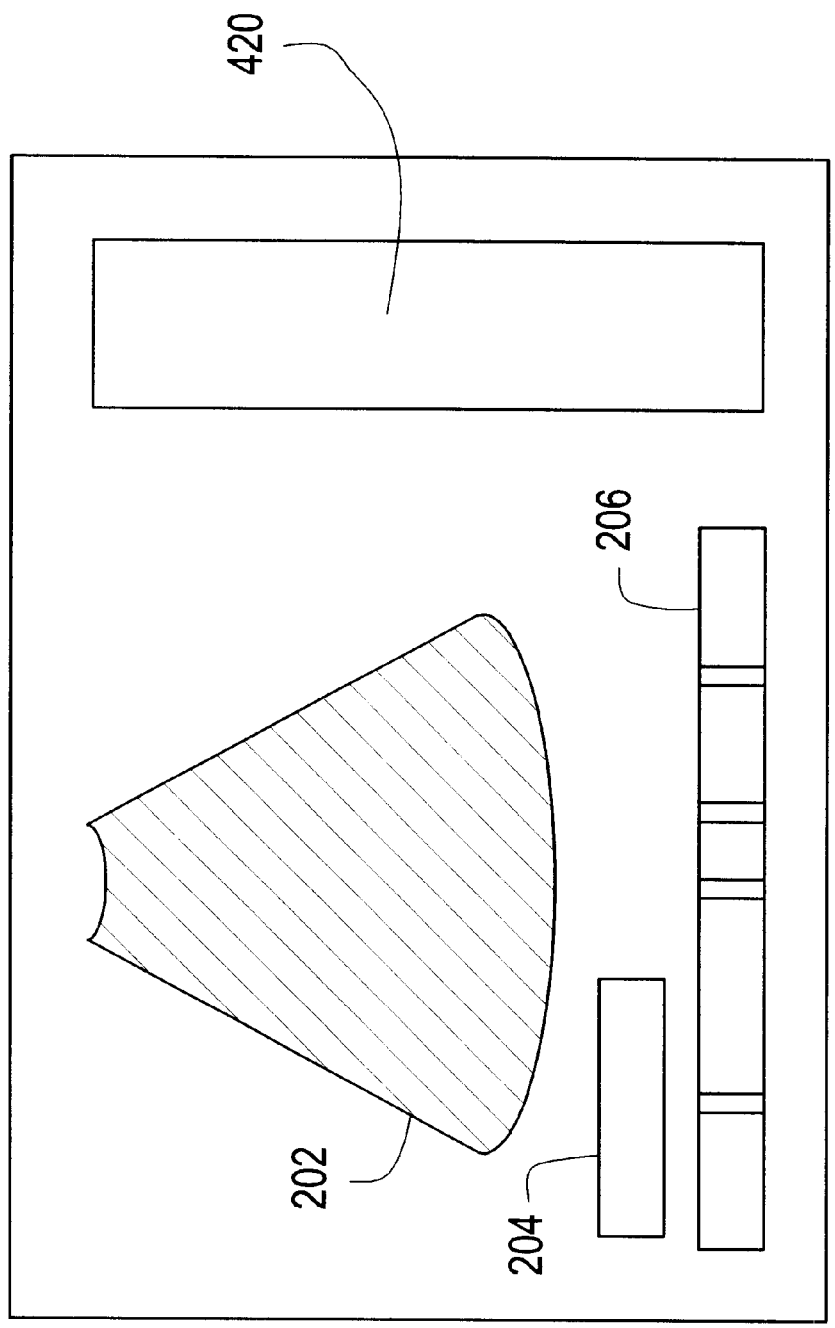
FIG. 7 shows a second exemplary screen displayed on the liquid crystal display device illustrated in FIGS. 1 and 2.

|  | First Display Mode | Second Display Mode |
| --- | --- | --- |
| CRT device | Display illustrated in FIG. 10 | Display illustrated in FIG. 10 |
| LCD device | Display illustrated in FIGS. 3 and 4 | Display illustrated in FIG. 7 (Display illustrated in FIG. 4 and Display illustrated in FIG. 10) |

The first display mode in the second embodiment is a display mode in which the screen illustrated in FIG. 10, i.e., a screen of "ultrasonic image information and its output status information", is displayed on the CRT device 30, and the screen relating to the operation of the ultrasonic diagnostic apparatus 100 exemplarily shown in FIG. 3, i.e., a screen of "ultrasonic processing, operation, status message/graphic display information not containing ultrasonic image information", is displayed on the LCD device 40.

The second display mode in the second embodiment is a display mode in which the screen illustrated in FIG. 10, i.e., a screen of "ultrasonic image information and its output status information", is displayed on the CRT device 30 as in the first display mode, and the image screen illustrated in FIG. 7 is displayed.

Specifically, on the CRT device 30, the display items illustrated in FIG. 10 (the "ultrasonic image information and its output status information" of the present invention) are displayed both in the first and second display modes.

On the other hand, on the LCD device 40, display items shown in FIG. 4 are displayed in the operation-related display region 420, and messages relating to the operation of the ultrasonic diagnostic apparatus 100 (the "ultrasonic processing, operation, status message/graphic display information not containing ultrasonic image information" of the present invention) are displayed in the items display region 410 as illustrated in FIG. 3, in the first display mode. In the second display mode, display in the operation-related display region 420 of FIG. 7 on the LCD device 40 is the same as the display items in FIG. 4 as in the first display mode; however, in the items display region 410, items illustrated in FIG. 10 (the "ultrasonic image information and its output status information" of the present invention) are displayed in the image display region 202, output status message display region 204 and cine gauge display region 206, as with the CRT device 30. The items displayed on the LCD device 40 in the second display mode will be referred to as "ultrasonic image information and its output status information, and ultrasonic processing, operation, status message/graphic display information" hereinbelow.

It should be noted that the display items illustrated in FIG. 10 displayed on the CRT device 30 and the items displayed in the items display region 410 on the LCD device 40 in the second display mode are completely the same in some cases, but they are not necessarily completely the same although similar to each other in other cases.

For example, the size of the display screen 200 of the CRT device 30 may be different from the size of the items display region 410 of the LCD device 40, and therefore, their display sizes may be different such that the size of display items illustrated in FIG. 10 displayed on the CRT device 30 is larger, and the size of items displayed in the items display region 410 of the LCD device 40 is smaller.

Moreover, the status of a display item illustrated in FIG. 10 displayed on the CRT device 30, for example, the output status in the region 204, may be different from the output status displayed in a portion of the items display region 410 that corresponds to the region 204 on the LCD device 40.

In the first embodiment, information relating to the ultrasonic diagnostic apparatus 100 was displayed on the CRT device 30, and operation commands were issued using the KB 31 or mouse 33. Therefore, operations by the operator were indirect, and ease of operation was lower. To improve those points in the second embodiment, it is made possible that operation commands relating to the ultrasonic diagnostic apparatus 100 are directly issued by the operator with the finger or pen using the touch panel 42 over the front surface of the display screen of the LCD device 40, and at the same time, the aforementioned zoom processing, measurement processing and the like may be done on an ultrasonic cross-sectional image displayed in the image display region 202.

Although details of operations in accordance with the second embodiment will be omitted, the second embodiment is different from the first embodiment in that the selection of the display item illustrated in FIG. 4 that was made on the CRT device 30 by the KB 31 or mouse 33 in the first embodiment is made by directly operating the touch panel 42 on the LCD device 40 with the finger or the like in the second embodiment.

Figure 5:
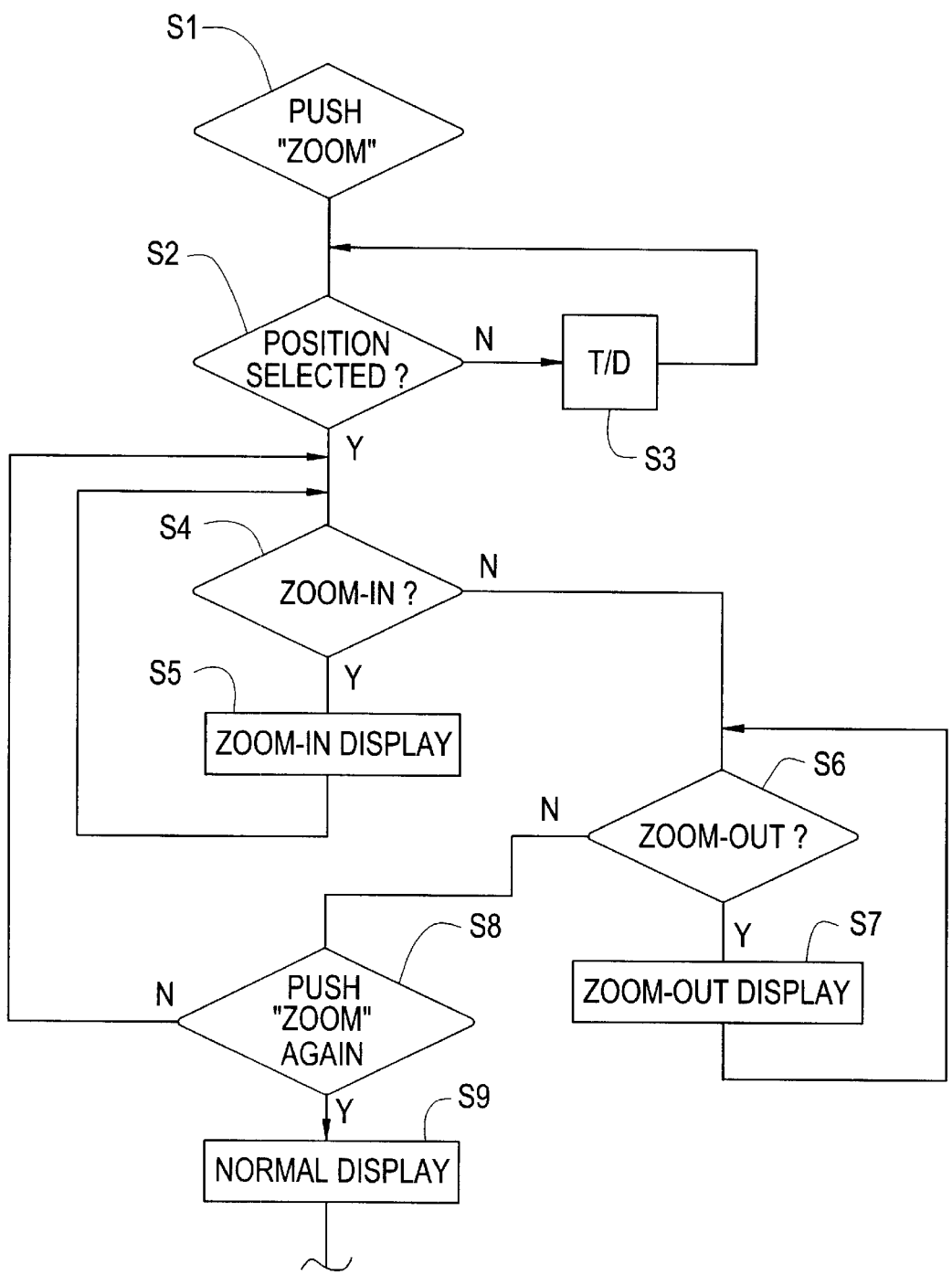
FIG. 5 is a flow chart showing details of first exemplary signal processing executed in the ultrasonic diagnostic apparatus illustrated in FIG. 1.
Figure 6:
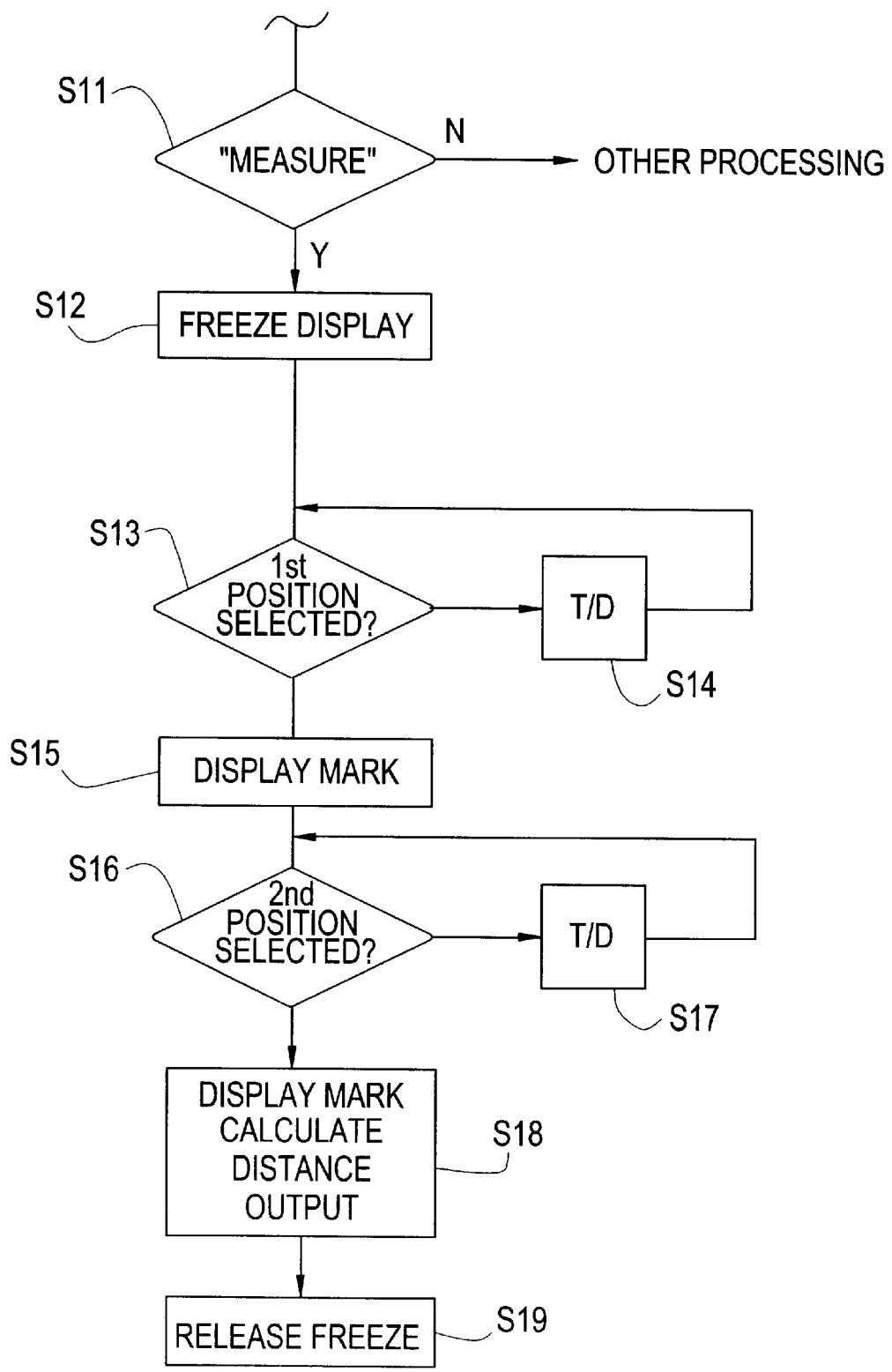
FIG. 6 is a flow chart showing details of second exemplary signal processing executed in the ultrasonic diagnostic apparatus illustrated in FIG. 1.

Taking the zoom processing as an example, in the zoom-in command in Step 4 in FIG. 5, the first video signal processing means 17 continuously performs zoom-in display at a certain rate while the operator presses the Zoom-in Display Select/Show portion 332; and the first video signal processing means 17 continuously performs zoom-out display at a certain rate while the operator presses the Zoom-out Display Select/Show portion 333. Such an operation is very friendly to the operator, thus further improving ease of operation.

In the second embodiment, the KB 31, trackball 32 and mouse 33 may be eliminated.

In the second embodiment, even when the zoom image is displayed in the image display region 202 of the LCD device 40, a normal ultrasonic cross-sectional image is displayed on the CRT device 30. Therefore, an ultrasonic diagnostic apparatus of the prior art may be used irrespective of additional operations such as zoom display or measurement display.

If an operation message is to be output to the LCD device 40 in the second embodiment, a margin beside the output status message display region 204 in the lower portion of the image display region 202, for example, may be used.

Third Embodiment

Figure 8:
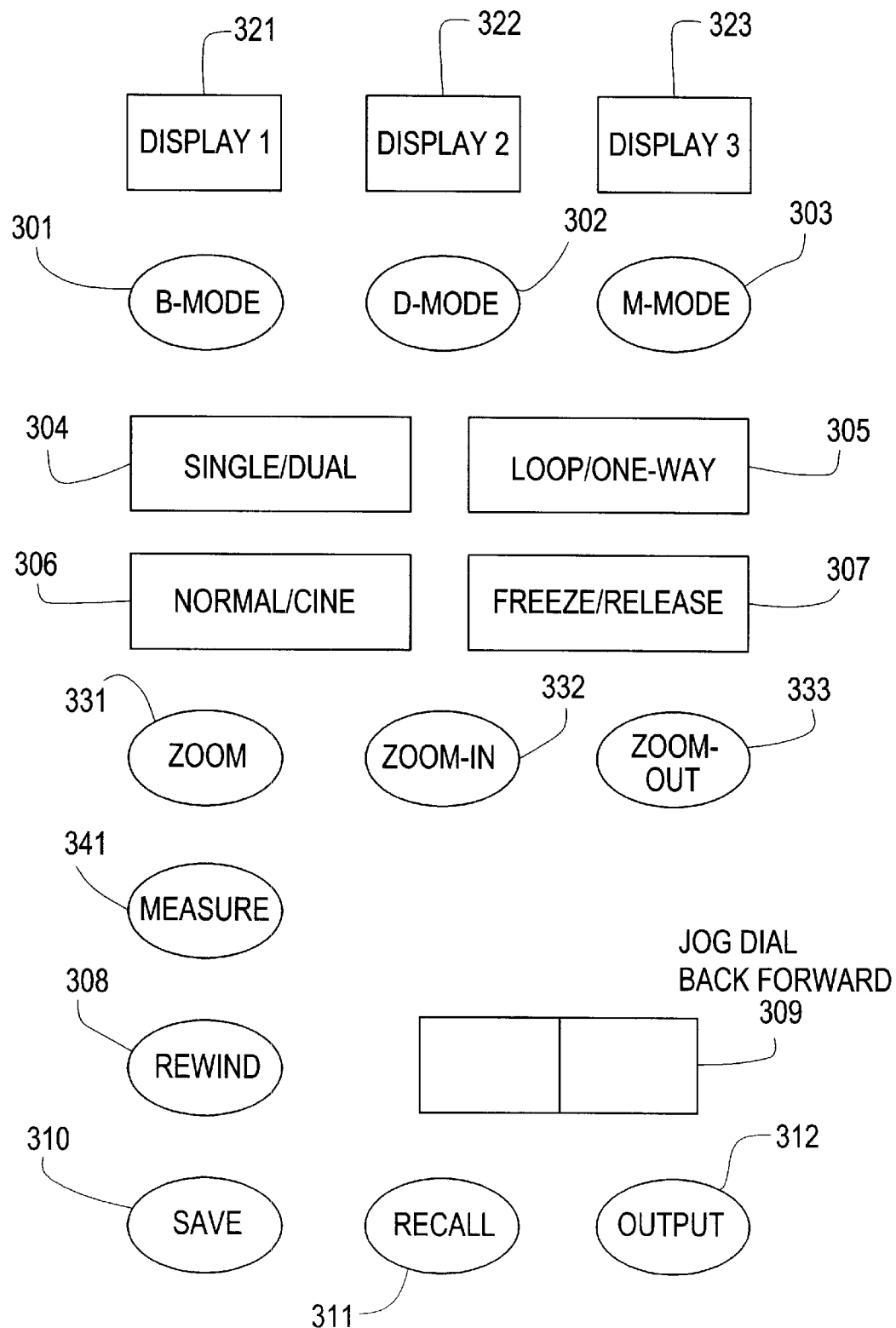
FIG. 8 is a second partial enlarged view of the screen illustrated in FIG. 3 displayed on the liquid crystal display device.

The number of display modes is not limited to two as described above, and three display modes may be defined as exemplarily shown in FIG. 8. FIG. 8 shows an exemplary display in the operation-related display region 420 of FIG. 3 or 7. The illustration of FIG. 8 is different from that of FIG. 4 in that a Third Display Mode Select/Show portion 323 is added.

The third embodiment combines the display modes in accordance with the first and second embodiments. Table 3 below shows an outline.

TABLE 3

| | CRT device 30 | LCD device 40 |
| --- | --- | --- |
| Display Mode 1 | Display of FIG. 10 | Display of FIGS. 3 and 8 |
| 2 | Display of FIGS. 3 and 8 | Display of FIG. 10 |
| 3 | Display of FIG. 10 | Display illustrated in FIG. 7 (Display illustrated in FIG. 8 and Display illustrated in FIG. 10) |

The display modes of the two display devices, i.e., the CRT device 30 and LCD device 40, are not limited to those in accordance with this embodiment, but several other display modes may be defined.

Fourth Embodiment

In addition to providing the touch panel 42 on the LCD device 40, the CRT device 30 may be provided with a touch panel similar to the touch panel 42 for directly making selections on the display of FIG. 4 displayed on the CRT device 30 using the touch panel on the CRT device 30 in the second display mode in the first embodiment, as with the touch panel 42 on the LCD device 40. In this case, the trackball 32 and mouse 33 are not required.

The zoom function and measurement function are presented by way of example: the functions are not limited thereto and several additional functions may be implemented.

Moreover, the operations illustrated in FIGS. 3, 4 and 11 are shown by way of example, and it is obvious to those skilled in the art that operations are not limited to such operations.

Although only part of the operations illustrated in FIGS. 4, 8 and 11 have been described, processing for these operations is achieved in the ultrasonic diagnostic apparatus 100 illustrated in FIG. 1 in a similar manner to the prior art, as generally described earlier.

Although the CRT device 30 is employed for the first display means and the LCD device 40 is employed for the second display means as an example, both the display means may be CRT devices or LCD devices, as described earlier.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnostic apparatus comprising:
   an arithmetic control/signal processing device for conducting arithmetic control and signal processing for ultrasonic diagnosis, and controlling display processing corresponding to at least first and second display modes;
   a storage device for storing ultrasonic reflection signals detected by an ultrasonic probe;
   a first display device capable of displaying graphics, messages and images;
   a second display device capable of displaying graphics, messages and images;
   a position detecting device for detecting a selected position in a display portion of said second display device;
   a first display processing device for conducting signal processing of the graphics, images and messages displayed on said first display device; and a second display processing device for conducting signal processing of the graphics, images and messages displayed on said second display device, wherein:

in the first display mode, said arithmetic control/signal processing device (a1) drives said first display processing device to display on said first display device ultrasonic image information and its output status information based on the ultrasonic reflection signals stored in said storage device, and (a2) drives said second display processing device to display on said second display device ultrasonic processing, operation, status message/graphic display information not containing said ultrasonic image information and its output status information, and conducts task processing for ultrasonic diagnosis in response to an operation detected by said position detecting device; and in the second display mode, said arithmetic control/signal processing device (b1) drives said first display processing device to display on said first display device ultrasonic processing, operation, status message/graphic display information not containing said ultrasonic image information and its output status information, and (b2) controls said second display processing device to display on said second display device said ultrasonic image information and its output status information based on the ultrasonic reflection signals stored in said storage device, and conducts processing in response to a position detection signal detected by said position detecting device.

2. The ultrasonic diagnostic apparatus of claim 1, wherein said processing in response to a position detecting signal detected by said position detecting device is zoom processing.

3. The ultrasonic diagnostic apparatus of claim 1, wherein said processing in response to a position detecting signal detected by said position detecting device is measurement processing.

4. The ultrasonic diagnostic apparatus of claim 1, wherein:

said position detecting device includes a touch panel.

5. The ultrasonic diagnostic apparatus of claim 1, wherein:

said first display device is a CRT device; and said second display device is a liquid crystal display device.

6. The ultrasonic diagnostic apparatus of claim 1, wherein:

said first display device is a CRT device; and said second display device is a CRT device.

7. The ultrasonic diagnostic apparatus of claim 1, wherein:

said first display device is a liquid crystal display device; and said second display device is a liquid crystal display device.

8. The ultrasonic diagnostic apparatus of claim 1, wherein:

said first display device is a liquid crystal display device; and said second display device is a CRT device.

9. An ultrasonic diagnostic apparatus comprising:

an ultrasonic arithmetic control/signal processing device for conducting arithmetic control and signal processing for ultrasonic diagnosis, and controlling display processing corresponding to at least first and second display modes;

a storage device for storing ultrasonic reflection signals detected by an ultrasonic probe;

a first display device capable of displaying graphics, messages and images;

a second display device capable of displaying graphics, messages and images;

a position detecting device for detecting a selected position in a display portion of said second display device;

a first display processing device for conducting signal processing of the graphics, images and messages displayed on said first display device; and a second display processing device for conducting signal processing of the graphics, images and messages displayed on said second display device, wherein:

in the first display mode, said arithmetic control/signal processing device (aa1) drives said first display processing device to display on said first display device ultrasonic image information and its output status information based on the ultrasonic reflection signals stored in said storage device, and (aa2) drives said second display processing device to display on said second display device ultrasonic processing, operation, status message/graphic display information not containing said ultrasonic image information and its output status information, and conducts task processing for ultrasonic diagnosis in response to an operation detected by said position detecting device; and in the second display mode, said arithmetic control/signal processing device (bb1) drives said first display processing device to display on said first display device ultrasonic processing, operation, status message/graphic display information not containing said ultrasonic image information and its output status information, and inputs an operation command corresponding to an operation via pointing device, and (bb2) drives said second display processing device to display on said second display device said ultrasonic image information and its output status information stored in said storage device, and conducts processing in response to a position detection signal detected by said position detecting device.

10. The ultrasonic diagnostic apparatus of claim 9, wherein said pointing device includes at least one of a keyboard, a trackball, and a mouse.

11. The ultrasonic diagnostic apparatus of claim 9, wherein said processing in response to a position detecting signal detected by said position detecting device is zoom processing.

12. The ultrasonic diagnostic apparatus of claim 9, wherein said processing in response to a position detecting signal detected by said position detecting device is measurement processing.

13. The ultrasonic diagnostic apparatus of claim 9, wherein:

said position detecting device includes a touch panel.

14. The ultrasonic diagnostic apparatus of claim 9, wherein:

said first display device is a CRT device; and said second display device is a liquid crystal display device.

15. The ultrasonic diagnostic apparatus of claim 9, wherein:
  said first display device is a CRT device; and
  said second display device is a CRT device.

16. The ultrasonic diagnostic apparatus of claim 9, wherein:
  said first display device is a liquid crystal display device; and
  said second display device is a liquid crystal display device.

17. The ultrasonic diagnostic apparatus of claim 9, wherein:
  said first display device is a liquid crystal display device; and
  said second display device is a CRT device.

18. An ultrasonic diagnostic apparatus comprising:
  an ultrasonic arithmetic control/signal processing device for conducting arithmetic control and signal processing for ultrasonic diagnosis, and controlling display processing corresponding to at least first and second display modes;
  a storage device for storing ultrasonic reflection signals detected by an ultrasonic probe;
  a first display device capable of displaying graphics, messages and images;
  a second display device capable of displaying graphics, messages and images;
  a position detecting device for detecting a selected position in a display portion of said second display device;
  a first display processing device for conducting signal processing of the graphics, images and messages displayed on said first display device; and
  a second display processing device for conducting signal processing of the graphics, images and messages displayed on said second display device, wherein:
    in the first display mode, said arithmetic control/signal processing device (aa1) drives said first display processing device to display on said first display device ultrasonic image information and its output status information based on the ultrasonic reflection signals stored in said storage device, and (aa2) drives said second display processing device to display on said second display device ultrasonic processing, operation, status message/graphic display information not containing said ultrasonic image information and its output status information, and conducts task processing for ultrasonic diagnosis in response to an operation detected by said position detecting device; and
    in the second display mode, said arithmetic control/signal processing device (aa1) drives said first display processing device to display on said first display device said ultrasonic image information and its output status information based on the ultrasonic reflection signals stored in said storage device, and (aa3) drives said second display processing device to display on part of said second display device said ultrasonic processing, operation, status message/graphic display information not containing said ultrasonic image information and its output status information, and to display on another part of said second display device information identical or similar to said ultrasonic image information and its output status information displayed on said first display device, and conducts processing in response to a position selection on said displayed image detected by said position detecting device.

19. The ultrasonic diagnostic apparatus of claim 18, wherein said processing in response to a position detecting signal detected by said position detecting device is zoom processing.

20. The ultrasonic diagnostic apparatus of claim 18, wherein said processing in response to a position detecting signal detected by said position detecting device is measurement processing.

21. The ultrasonic diagnostic apparatus of claim 18, wherein:
  said position detecting device includes said touch panel.

22. The ultrasonic diagnostic apparatus of claim 18, wherein:
  said first display device is a CRT device; and
  said second display device is a liquid crystal display device.

23. The ultrasonic diagnostic apparatus of claim 18, wherein:
  said first display device is a CRT device; and
  said second display device is a CRT device.

24. The ultrasonic diagnostic apparatus of claim 18, wherein:
  said first display device is a liquid crystal display device; and
  said second display device is a liquid crystal display device.

25. The ultrasonic diagnostic apparatus of claim 18, wherein:
  said first display device is a liquid crystal display device; and
  said second display device is a CRT device.

* * * * *

UNITED STATES PATENT AND TRADEMARK OFFICE
CERTIFICATE OF CORRECTION

PATENT NO. : 6,605,040 B2
DATED : August 12, 2003
INVENTOR(S) : Tsutomu Yawata et al.

It is certified that error appears in the above-identified patent and that said Letters Patent is hereby corrected as shown below:

Column 24,
Line 29, delete "said touch panel" insert therefor -- a touch panel --

Signed and Sealed this

Sixth Day of January, 2004

JAMES E. ROGAN
*Director of the United States Patent and Trademark Office*